United States Patent
Schebesta et al.

(10) Patent No.: US 7,671,984 B2
(45) Date of Patent: Mar. 2, 2010

(54) SPECTROMETRIC MEASURING PROBE AND METHOD FOR RECALIBRATING THE SAME

(75) Inventors: Wilhelm Schebesta, Jena (DE); Werner Hoyme, Gebstedt (DE); Michael Rode, Jena (DE); Nico Correns, Weimar (DE); Martin Goetz, Jena (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 0 days.

(21) Appl. No.: 11/587,453

(22) PCT Filed: Apr. 26, 2005

(86) PCT No.: PCT/EP2005/004433

§ 371 (c)(1),
(2), (4) Date: Oct. 24, 2006

(87) PCT Pub. No.: WO2005/106431

PCT Pub. Date: Nov. 10, 2005

(65) Prior Publication Data

US 2007/0236692 A1  Oct. 11, 2007

(30) Foreign Application Priority Data

Apr. 30, 2004 (DE) .................. 10 2004 021 448
Sep. 30, 2004 (DE) .................. 10 2004 048 102

(51) Int. Cl.
    G01J 3/28       (2006.01)
(52) U.S. Cl. ........................................ 356/326
(58) Field of Classification Search .......... 356/326–328
    See application file for complete search history.

(56) References Cited

U.S. PATENT DOCUMENTS

| 4,029,419 | A | 6/1977 | Schumann, Jr. et al. |
| 5,982,501 | A | 11/1999 | Benz et al. |
| 7,265,831 | B2 * | 9/2007 | Kormann et al. ............ 356/328 |
| 2001/0055116 | A1 * | 12/2001 | Maczura et al. ............. 356/326 |
| 2002/0179710 | A1 * | 12/2002 | Gu et al. ..................... 235/454 |

FOREIGN PATENT DOCUMENTS

| DE | 10 2004 021 448 | 11/2005 |
| EP | 0 296 259 | 12/1988 |
| WO | 00/04373 | 1/2000 |

\* cited by examiner

Primary Examiner—Kara E Geisel
(74) Attorney, Agent, or Firm—Reed Smith LLP

(57) ABSTRACT

An arrangement for measuring the diffuse reflection of samples and a method for internal recalibration of the measuring head. The spectrometric measuring head with a device for recalibration comprises a housing which is provided with a window and which contains an illumination source, a spectrometer arrangement and at least two standards for internal recalibration. The two standards can be swiveled into the beam path of the measuring head selectively so that the measurement light emitted by the illumination source can be used in its entirety for recalibration. A processor for acquiring and processing measured values and an interface to a bus system are arranged in the housing. Accordingly, relatively time-consuming calibration of the measuring head at the place of use is required only before putting into operation or at longer time intervals. By the internal recalibrations, it is possible to prevent changes in the measured values in long-term operation.

21 Claims, 2 Drawing Sheets

SPECTROMETRIC MEASURING PROBE AND METHOD FOR RECALIBRATING THE SAME

CROSS-REFERENCE TO RELATED APPLICATIONS

Figure 1:
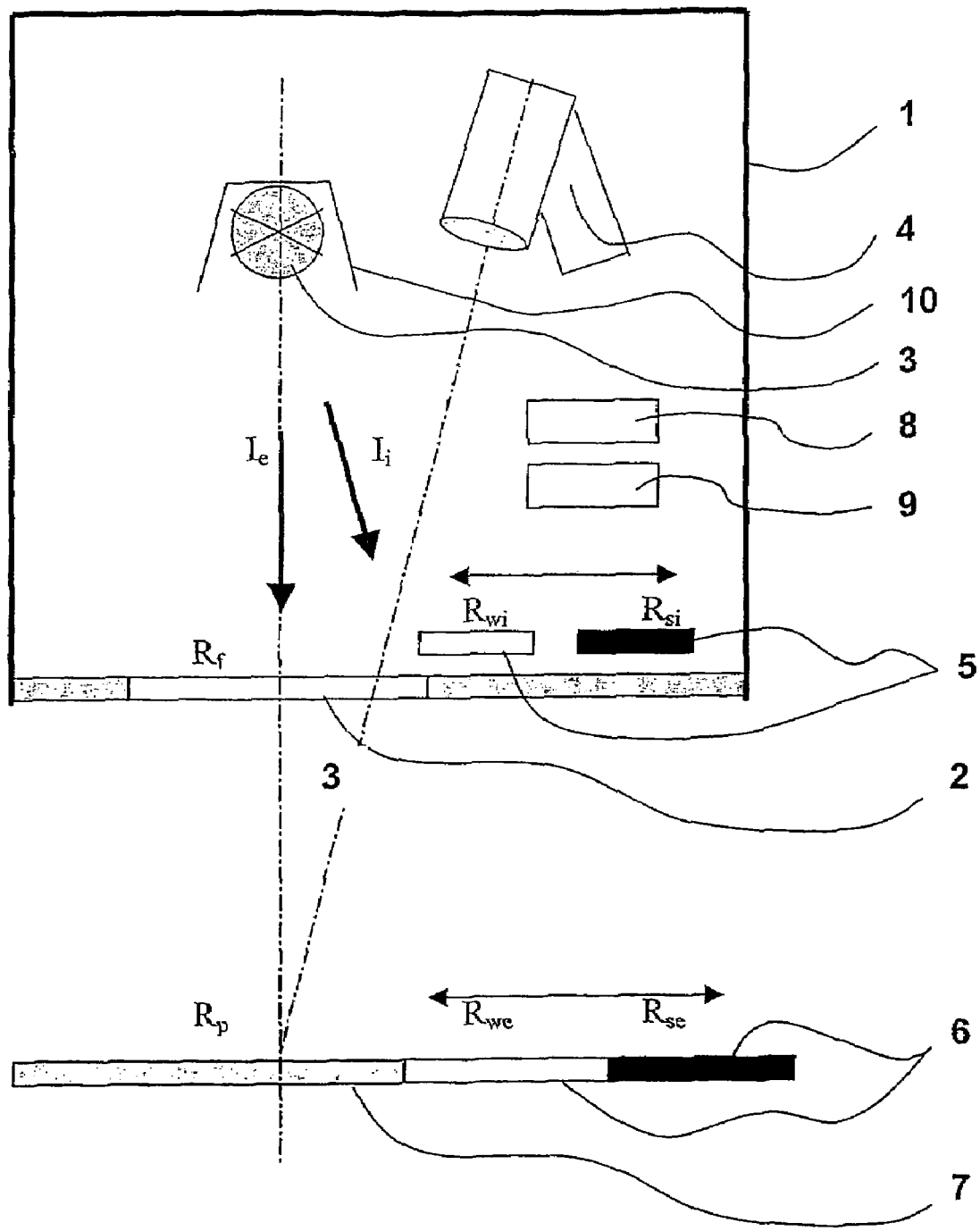

This application claims priority of International Application No. PCT/EP2005/004433, filed Apr. 26, 2005 and German Application No. 10 2004 021 448.4, filed Apr. 30, 2004 and German Application No. 10 2004 048 102.4, filed Sep. 30, 2004, the complete disclosures of which are hereby incorporated by reference.

BACKGROUND OF THE INVENTION a) Field of the Invention

The present invention is directed to an arrangement for measuring the diffuse reflection of samples, particularly in process measurement technique, and to a method for the internal recalibration of the measuring head.

b) Description of the Related Art

Numerous solutions using spectrometric arrangements for process monitoring are known from the prior art. While no problems arise from measurements under laboratory conditions when standardized conditions are maintained, measurement tasks in process monitoring are subject to special requirements.

Measuring heads for the measurement of diffuse reflections require the two standards, black and white, as measuring means for calibration. The measurement scale is calibrated at the start of the measurement by means of these two standards. The samples to be measured subsequently fall between the two limiting values. Any changes in the measurement conditions can lead to erroneous results.

For example, such changes may result from deposits on the light source due to aging so that the intensity and color temperature of the light can change. Further, thermal influences on the detection system are also possible. These can lead to variations in sensitivity and in the dark signal and can accordingly falsify the measurement results. To prevent this, it is necessary to recalibrate at regular time intervals with the above-mentioned two standards.

As a rule, the measurement sample must be removed from the sample plane and replaced by the two calibrating standards. In process measurement technology this process is not only disruptive and time-consuming but, in some cases, cannot even be implemented. Another possibility consists in positioning the measuring head exactly over the calibrating sample at a location other than the sample measurement location.

U.S. Pat. No. 5,982,501 A describes a device for measuring the reflectivity of a sample whose measured values are preferably fed to a spectrometer. The measurement device comprises a housing enclosing a measuring head for measuring the light reflected by the object, an opto-electric converter for converting the measured light into electrical signals, a computer unit for processing the electrical signals and for controlling the device, a display unit for displaying the measured values, and an operating unit. When the measurement process is initiated, the measuring head is displaced by a motor from its rest position in the housing to the measurement position outside the housing, and the measurement is carried out. The measuring head then moves to the rest position in the housing again. Reference patterns for calibrating the measuring head are arranged inside the housing. For this purpose, the measuring head is positioned over the respective reference pattern and the corresponding measurement is initiated. It is possible to calibrate based on the reference values stored in the computer unit. Other color standards can be used in addition to a white standard as reference patterns for checking the spectral calibration. Further, the arrangement has a filter wheel which can be displaced together with the measuring head to spectrally influence either the light of the measurement light source or the light reflected by the object. For this purpose, the filters of the filter wheel are positioned in the respective beam path. This solution is disadvantageous in that the calibration takes place in the housing rather than directly at the measurement location. The results of the calibrations can be transferred from the interior of the housing to the external measurement location only with difficulty due to the correspondingly different conditions. Further, the entire measuring head must be exactly positioned on the calibration standard and on the measurement sample by motor in this solution.

A method and a corresponding arrangement for automatic calibration of a color detection system is described in EP 0 010 940 A1. The solution is used to monitor the color of a product and/or use it as a criterion for sorting. The principal areas of application are, for example, monitoring fried potato chips or sorting fruits or vegetables. For this purpose, the products are illuminated by light of a defined wavelength, and the light reflected by the products is evaluated. The solution describes an automatic calibration method for compensating for the influence of fluctuations in color temperature of the light source or random changes in the measurement process. To calibrate the arrangement, a disk with a known color pattern is swiveled in front of the measuring head and the intensity of the reflected light is measured. The measured light signal is compared to a known standard signal so that changes can be determined. This solution is disadvantageous in that it lacks the universality that is only ensured by the spectral information. The color patterns used for calibration are specific to the application.

Patent Application DE 10 2004 021 448.4, which has not yet been published, describes a spectrometric reflection measuring head with internal recalibration in which at least two standards, preferably a black standard and a white standard, are additionally provided in the housing of the measuring head for internal recalibration and can be swiveled selectively into the beam path of the reflection measuring head. After the measurement data of the two standards is acquired by the spectrometer, the recalibration of the reflection measuring head is carried out by the spectrometer by means of the controlling and evaluating unit. In addition, at least two external standards can be provided for calibrating the reflection measuring head before putting the measuring arrangement into operation or at determined time intervals.

OBJECT AND SUMMARY OF THE INVENTION

It is the primary object of the present invention to provide an arrangement for spectrometric reflection measurement in which changes in the system can be compensated automatically at determinable time intervals by recalibration based on existing universal reference patterns without changing the measuring arrangement for this purpose.

This object is met according to the invention by a spectrometric measuring head with recalibration means comprising a housing which is provided with a window. Arranged in the housing are a spectrometer arrangement and at least two standards for internal recalibration. The standards are adapted to being swiveled into the beam path of the measuring head selectively in such a way that the measurement light emitted by the illumination source is used in its entirety for recalibration and processing the measured values and an interface to a bus system are also arranged in the housing.

The spectrometric measuring head with means for recalibration comprises a housing which is provided with a window and which contains an illumination source, a spectrometer arrangement and at least two standards for recalibration. The two standards can be swiveled into the beam path of the measuring head selectively in such a way that the measurement light emitted by the illumination source can be used in its entirety for recalibration. Further, a processor for acquiring and processing the measured values and an interface to a bus system are provided in the housing.

The proposed technical solution can be commercially applied for specific measurement tasks in the VIS and NIR range. While the determination of the color of continuous samples is carried out in the VIS range, for example, content of moisture, fat, starch, protein, and the like for agricultural and food samples is determined in the NIR range. The spectrometers to be used are adapted in a corresponding manner for using different spectral ranges; the measuring head can be used for the entire spectral region.

The invention will be described in the following with reference to an embodiment example.

IN THE DRAWINGS

Figure 2:
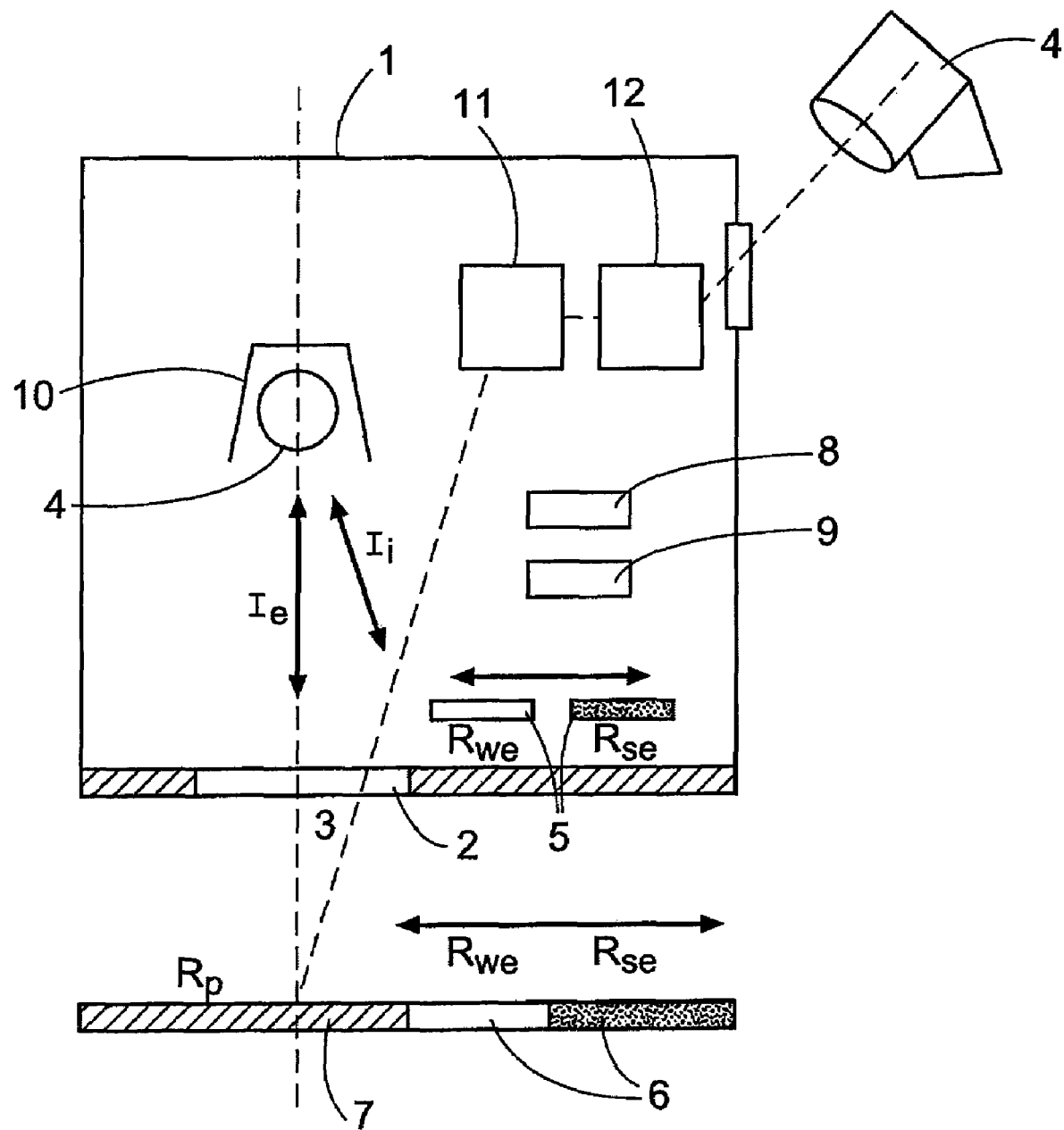

FIG. 1 is a schematic view of the construction of the spectrometric reflection measuring head according to the invention; and FIG. 2 is a schematic view of an alternative construction in accordance with the invention.

DESCRIPTION OF THE PREFERRED EMBODIMENTS

FIG. 1 shows the spectrometric measuring head with means for recalibration according to the invention. It comprises a housing 1 which is provided with a window 2 and in which are arranged an illumination source 3, a spectrometer arrangement 4, and at least two standards 5 for recalibrating. These standards 5 can be swiveled into the beam path of the measuring head selectively in such a way that the measurement light emitted by the illumination source 3 is used in its entirety for recalibration. In addition, a processor 8 for acquiring and processing the measured values and an interface 9 to a bus system are provided in the housing 1.

In another construction, an optical assembly 11 is provided instead of the spectrometer arrangement 4 for collecting the measurement light and for coupling it into a light guide 12 which conducts the measurement light to the spectrometer arrangement 4.

In order to adapt the spectrometer arrangement to the different reflection behavior of various samples 7, the lamp output of the illumination source 3, which preferably has a reflector 10, can be regulated automatically. This ensures that the integration time of the spectrometer arrangement 4 remains virtually constant. In connection with referencing, a measurement which is optimized with respect to the respective sample conditions and measurement conditions can accordingly be carried out at any time.

The spectrometer arrangement 4 comprises at least one dispersion element and a detector array and may also have imaging optics assemblies if required. By directly imaging the radiation reflected by the sample 7 on the detector array, images from the structure of the sample 7 on the detector array can lead to measurement errors depending on the sample 7. A light integrator is provided in order to prevent this.

The two standards 5 provided in the measuring head are used for internal recalibration of the measuring arrangement. At least two additional external standards 6 are provided for calibrating the measuring head before putting the measuring arrangement into operation or at determined time intervals. Black and white standards are preferably used as internal standards 5 and also as external standards 6 and can be supplemented by additional, application-specific internal standards for more extensive recalibration.

The standards 5 and 6 are preferably actuated by motor and can be controlled automatically and/or manually. The internal and external referencing enables automatic system monitoring, monitoring of the window 2 for damage, soiling, etc. and also makes it possible to use different window material without having to change or adapt the existing calibration.

After the measurement data is acquired with the two internal standards 5 by the spectrometer arrangement 4, the recalibration of the measuring head is carried out using the values measured in the calibration of the reflection measuring head before putting into operation. After the internal standard 5 has been swiveled out of the beam path, the measuring head is ready for the next measurement of the sample.

Further, a processor 8 for acquiring and processing the measured values is arranged in the housing 1. Raw data, i.e., preprocessing of data based on spectra, and calculated results can be generated by this processor 8 and can then be transmitted to a bus system via the interface 9. Further, the processor 8 contains the software for the required bus management. The processor 8 provides for a fully autarchic system. In order that the measuring head can be used within a wide range of operating temperatures without additional cooling of the detector array, the processor 8 contains corresponding compensating electronics which compensate for the changing parameters of the spectrometer arrangement 4 during changes in temperature.

The interface 9 to a bus system is used for data transfer and/or calibration and/or system diagnosis and can be hardwired or wireless.

In the method for recalibrating a spectrometric measuring head in which an illumination source 3, a spectrometer arrangement 4 and at least two standards 5 for recalibration are arranged in a housing 1 provided with a window 2, these standards 5 are selectively swiveled into the beam path of the measuring head in such a way that the measurement light emitted by the illumination source 3 is used in its entirety for recalibration. The measured values are acquired and processed by a processor 8 and are transmitted to a bus system via an interface 9.

In the spectrometric measuring head according to the invention, the sample 7 to be measured is irradiated by an illumination source 3. The radiation reflected by the sample 7 is received directly by a spectrometer arrangement 4. Different contents can be determined using the intensity distribution of the reflected radiation based on calibrations. It is possible to use the measuring head described herein to carry out random measurements as well as measurements of a material flow.

The measured intensity values required for the different internal standards 5 and external standards 6 are stored and used for recalibration. The required intensity values are:

external white standard $I_{we}=I_e \cdot (R_f+R_{we} \cdot [1-R_f]^2)+I_d$ external black standard $I_{se}=I_e \cdot (R_f+R_{se} \cdot [1-R_f]^2)+I_d$ internal white standard $I_{wi}=I_i \cdot R_{wi}+I_d$ internal black standard $I_{si}=I_i \cdot R_{si}+I_d$ and the sample is: $I_p=I_e \cdot (R_f+R_p \cdot [1-R_f]^2)+I_d$, where $I_e$ is the measurement intensity at the external measurement location $I_i$ is the measurement intensity at the internal measurement location $I_d$ is the measurement intensity of the dark signal
$R_f$ is the reflectance of the measuring head window
$R_{we}$ is the reflectance of the external white standard
$R_{se}$ is the reflectance of the external black standard
$R_{wi}$ is the reflectance of the internal white standard
$R_{si}$ is the reflectance of the internal black standard
$R_p$ is the reflectance of the measurement sample.

By subtractions $D_1$ to $D_4$, compensation of the change in the dark signal $I_d$ is updated with every internal recalibration.

$D_1=I_{we}-I_{se}=I_e \cdot [1-R_f]^2 \cdot (R_{we}-R_{se})$ $D_2=I_{wi}-I_{si}=I_i \cdot (R_{wi}-R_{si})$ $D_3=I_{se}-I_{si}=I_e \cdot (R_f+R_{se} \cdot [1-R_f]^2)-I_i \cdot R_{si}$ $D_4=I_p-I_{si}=I_e \cdot (R_f+R_p \cdot [1-R_f]^2)-I_i \cdot R_{si}$ The quotient $q(t)=D_2/D_2(t)=I_e/I_e(t)=I_i/I_i(t)$ describes the relative time change in the sensitivity and measurement intensity at the times when $D_2$ is measured (at the start) and when $D_2(t)$ is measured (after recalibration). The general design of the measuring head ensures that q(t) is the same at the internal measurement location and at the external measurement location.

The reflectance $R_p'$ (at the start) and the corrected reflectance $R_p'(t)$ (after recalibration) of the measurement sample can be calculated from these values.

$$R_p' = \frac{D_4 - D_3}{D_1} = \frac{R_p - R_{se}}{R_{we} - R_{se}}$$

$$R_p'(t) = \frac{D_4(t)*q(t) - D_3}{D_1} = \frac{R_p - R_{se}}{R_{we} - R_{se}}$$

The result $R_p'(t)$ is not affected by the changes over time in the dark signal, lamp intensity and receiver sensitivity.

After the internal standard 5 has been swiveled out of the beam path, the measuring head is ready for the next measurement of the sample 7.

The internal standards 5 can be arranged on a filter wheel or on a slide mechanism, for example. In addition to the black and white standards, additional internal standards can be provided for application-specific recalibration.

Although the measurement intensities of the illumination source 3 at the internal measurement location are different than those at the external sample measurement location, the geometric arrangement of the internal standards 5 ensures that changes in spectral intensity take place with identical proportionality at both measurement locations. Changes in sensitivity and in the dark signal of the spectrometer arrangement 4 are not dependent on the measurement location and are accordingly identical internally and externally. Accordingly, a change in the measured value caused by the above-mentioned influences can be prevented over long-term operation by recalibration carried out at established time intervals.

In the solution according to the invention, the internal recalibration is carried out automatically at short time intervals according to a previously established schedule or as needed.

Both the measuring head and the measured object remain in the normal measurement position during calibration and recalibration.

In the solution according to the invention, the relatively time-consuming calibration of the measuring head at the place of use is required only before putting into operation or at longer time intervals. By means of the internal recalibrations to be carried out at fixed time intervals, it is possible to prevent changes in the measured values in long-term operation which may be caused, for example, by changes in sensitivity and changes in the dark signal of the detection system or by fluctuating light intensity of the illumination source.

While the foregoing description and drawings represent the present invention, it will be obvious to those skilled in the art that various changes may be made therein without departing from the true spirit and scope of the present invention.

The invention claimed is:

1. A spectrometric measuring head with recalibration means, the measuring head comprising:
   a housing which is provided with a window to an external measurement location;
   arranged in said housing are an illumination source, a spectrometer arrangement and at least two standards for internal recalibration;
   said standards adapted to being swiveled into the beam path to an internal measurement location of the measuring head selectively;
   a processor for acquiring and processing measured values and an interface to a bus system, also being arranged in the housing; and
   a controlling and evaluating unit which recalibrates the spectral measuring head by using:
   a) intensity values for internal standards measured at the internal measurement location; and
   b) intensity values for at least two additional external standards measured at the external measurement location;
   wherein one of the two internal standards is a light internal standard, and the other of the two internal standards is a dark internal standard;
   wherein one of the two external standards is a light external standard, and the other of the two internal standards is a dark external standard; and
   wherein a reflectance $R_p'$ (at the start) and the corrected reflectance $R_p'(t)$ (after recalibration) of the measurement sample is calculated from the following formulas:

$$R_p' = \frac{D_4 - D_3}{D_1} = \frac{R_p - R_{se}}{R_{we} - R_{se}}; \text{ and}$$

$$R_p'(t) = \frac{D_4(t)*q(t) - D_3}{D_1} = \frac{R_p - R_{se}}{R_{we} - R_{se}};$$

where:
$R_f$ is the reflectance of the window:
$R_{we}$ is the reflectance of the external light standard;
$R_{se}$ is the reflectance of the external dark standard;
$R_{wi}$ is the reflectance of the internal light standard;
$R_{si}$ is the reflectance of the internal dark standard; and
$R_p$ is the reflectance of a measurement sample;
where the quotient q(t) is calculated by the following formula:

$q(t)=D_2/D_2(t)=I_e/I_e(t)=I_i/I_i(t)$;

where $D_1$ to $D_4$ are calculated by the following formulas:

$$D_1 = I_{we} - I_{se} = I_e \cdot [1-R_f]^2 \cdot (R_{we} - R_{se});$$

$$D_2 = I_{wi} - I_{si} = I_i \cdot (R_{wi} - R_{si});$$

$$D_3 = I_{se} - I_{si} = I_e \cdot (R_f + R_{se} \cdot [1-R_f]^2) - I_i \cdot R_{si}; \text{ and}$$

$$D_4 = I_p - I_{si} = I_e \cdot (R_f + R_p \cdot [1-R_f]^2) - I_i \cdot R_{si};$$

where:
$I_e$ is the measurement intensity at the external measurement location;
$I_i$ is the measurement intensity at the internal measurement location; and
$I_d$ is the measurement intensity of a dark signal; and where $I_{we}$, $I_{se}$, $I_{wi}$, $I_{si}$, and $I_p$ are calculated by the following formulas:

$$I_{we} = I_e \cdot (R_f + R_{we} \cdot [1-R_f]^2) + I_d;$$

$$I_{se} = I_e \cdot (R_f + R_{se} \cdot [1-R_f]^2) + I_d;$$

$$I_{wi} = I_i \cdot R_{wi} + I_d;$$

$$I_{si} = I_i \cdot R_{si} + I_d; \text{ and}$$

$$I_p = I_e \cdot (R_f + R_p \cdot [1-R_f]^2) + I_d.$$

2. The spectrometric measuring head according to claim 1; wherein at least two additional external standards are provided for calibrating the measuring head before putting the measuring arrangement into operation or at determined time intervals.

3. The spectrometric measuring head according to claim 1; wherein the internal standards and/or external standards are/is black and white standards and are actuated by motor and wherein said motor can be controlled automatically and/or manually.

4. The spectrometric measuring head according to claim 1; wherein additional, application-specific internal standards are provided for more extensive recalibration.

5. The spectrometric measuring head according to claim 1; wherein the interface to a bus system is provided for data transfer and/or calibration and/or system diagnosis.

6. A spectrometric measuring system including a measuring head with recalibration means, the measuring head comprising:
a housing which is provided with a window to an external measurement location;
arranged in said housing are an illumination source, an optical assembly being provided in the housing for collecting measurement light and for coupling it into a light guide, and at least two standards for internal recalibration;
said measurement light being guided via said light guide to a spectrometer arrangement arranged outside of the measuring head;
said housing having connections to a voltage source, and to a controlling and evaluating unit;
said two standards provided in the housing being adapted to being selectively swiveled into the beam path to an internal measurement location of the measuring head for internal recalibration; and
a processor for acquiring and processing the measured values and an interface to a bus system;
wherein the controlling and evaluating unit recalibrates the spectrometric measuring system by using:
a) intensity values for internal standards measured at the internal measurement location; and
b) intensity values for at least two additional external standards measured at the external measurement location.

7. A method for recalibrating a spectrometric measuring head in which an illumination source, a spectrometer arrangement and at least two internal standards for recalibration are arranged in a housing provided with a window to an external measurement location, said method comprising the steps of:
selectively swiveling said standards to an internal measurement location in the beam path of the measuring head;
measuring intensity values for the internal standards; and
carrying out the recalibration using:
a) the intensity values for the internal standards; and
b) intensity values for at least two additional external standards measured at the external measurement location;
wherein one of the two internal standards is a light internal standard, and the other of the two internal standards is a dark internal standard;
wherein one of the two external standards is a light external standard, and the other of the two internal standards is a dark external standard; and
wherein a reflectance $R_p'$ (at the start) and the corrected reflectance $R_p'(t)$ (after recalibration) of the measurement sample is calculated from the following formulas:

$$R_p' = \frac{D_4 - D_3}{D_1} = \frac{R_p - R_{se}}{R_{we} - R_{se}}; \text{ and}$$

$$R_p'(t) = \frac{D_4(t) * q(t) - D_3}{D_1} = \frac{R_p - R_{se}}{R_{we} - R_{se}};$$

where:
$R_f$ is the reflectance of the window;
$R_{we}$ is the reflectance of the external light standard;
$R_{se}$ is the reflectance of the external dark standard;
$R_{wi}$ is the reflectance of the internal light standard;
$R_{si}$ the reflectance of the internal dark standard; and
$R_p$ is the reflectance of a measurement sample;
where the Quotient q(t) is calculated by the following formula:

$$q(t) = D_2/D_2(t) = I_e/I_e(t) = I_i/I_i(t);$$

where $D_1$ to $D_4$ are calculated by the following formulas:

$$D_1 = I_{we} - I_{se} = I_e \cdot [1-R_f]^2 \cdot (R_{we} - R_{se});$$

$$D_2 = I_{wi} - I_{si} = I_i \cdot (R_{wi} - R_{si});$$

$$D_3 = I_{se} - I_{si} = I_e \cdot (R_f + R_{se} \cdot [1-R_f]^2) - I_i \cdot R_{si}; \text{ and}$$

$$D_4 = I_p - I_{si} = I_e \cdot (R_f + R_p \cdot [1-R_f]^2) - I_i \cdot R_{si};$$

where:
$I_e$ is the measurement intensity at the external measurement location;
$I_i$ is the measurement intensity at the internal measurement location; and
$I_d$ is the measurement intensity of a dark signal; and where $I_{we}$, $I_{se}$, $I_{wi}$, $I_{si}$, and $I_p$ are calculated by the following formulas:

$$I_{we} = I_e \cdot (R_f + R_{we} \cdot [1-R_f]^2) + I_d;$$

$$I_{se} = I_e \cdot (R_f + R_{se} \cdot [1-R_f]^2) + I_d;$$

$$I_{wi} = I_i \cdot R_{wi} + I_d;$$

$$I_{si} = I_i \cdot R_{si} + I_d; \text{ and}$$

$$I_p = I_e \cdot (R_f + R_p \cdot [1-R_f]^2) + I_d.$$

8. The method for recalibration according to claim 7;
wherein at least two external standards are selectively swiveled into the beam path of the measuring head for calibrating the measuring head before putting the measuring arrangement into operation or at determined time intervals.

9. The method for recalibration according to claim 7;
wherein the recalibration by means of internal standards and/or external standards, including black and white standards, is carried out automatically according to a previously established schedule or as needed.

10. The method for recalibration according to claim 7;
wherein the interface is provided at a bus system for data transfer and/or calibration and/or system diagnosis.

11. A method for recalibrating a spectrometric measuring head in which an illumination source, a spectrometer arrangement and at least two internal standards for recalibration are arranged in a housing provided with a window to an external measurement location, said method comprising the steps of:
selectively swiveling said standards to an internal measurement location in the beam path of the measuring head;
measuring intensity values for the internal standards; and
carrying out the recalibration using:
a) the intensity values for the internal standards; and
b) intensity values for at least two additional external standards measured at the external measurement location;
wherein an optical assembly instead of the spectrometer arrangement is provided in the housing for collecting the measurement light and for coupling it into a light guide, the measurement light is guided via this light guide to a spectrometer arrangement arranged outside of the measuring head, and the housing has connections to a voltage source, and to a controlling and evaluating unit.

12. The method for internal recalibration according to claim 7;
wherein additional, application-specific internal standards are provided for more extensive recalibrations.

13. The spectrometric measuring head according to claim 1;
wherein the quotient q(t) is the same value at the internal measurement location and at the external measurement location.

14. The spectrometric measuring system according to claim 6;
wherein one of the two internal standards is a light internal standard, and the other of the two internal standards is a dark internal standard;
wherein one of the two external standards is a light external standard, and the other of the two internal standards is a dark external standard; and
wherein a reflectance $R_p'$ (at the start) and the corrected reflectance $R_p'(t)$ (after recalibration) of the measurement sample is calculated from the following formulas:

$$R_p' = \frac{D_4 - D_3}{D_1} = \frac{R_p - R_{se}}{R_{we} - R_{se}}; \text{ and}$$

$$R_p'(t) = \frac{D_4(t) * q(t) - D_3}{D_1} = \frac{R_p - R_{se}}{R_{we} - R_{se}};$$

where:
$R_f$ is the reflectance of the window;
$R_{we}$ is the reflectance of the external light standard;
$R_{se}$ is the reflectance of the external dark standard;
$R_{wi}$ is the reflectance of the internal light standard;
$R_{si}$ the reflectance of the internal dark standard; and
$R_p$ is the reflectance of a measurement sample;
where the quotient q(t) is calculated by the following formula:

$$q(t)=D_2/D_2(t)=I_e/I_e(t)=I_i/I_i(t);$$

where the $D_1$ to $D_4$ are calculated by the following formulas:

$$D_1=I_{we}-I_{se}=I_e \cdot [1-R_f]^2 \cdot (R_{we}-R_{se});$$

$$D_2=I_{wi}-I_{si}=I_i \cdot (R_{wi}-R_{si});$$

$$D_3=I_{se}-I_{si}=I_e \cdot (R_f+R_{se} \cdot [1-R_f]^2)-I_i \cdot R_{si}; \text{ and}$$

$$D_4=I_p-I_{si}=I_e \cdot (R_f+R_p \cdot [1-R_f]^2)-I_i \cdot R_{si};$$

where:
$I_e$ is the measurement intensity at the external measurement location;
$I_i$ is the measurement intensity at the internal measurement location; and
$I_d$ is the measurement intensity of a dark signal; and
where $I_{we}, I_{se}, I_{wi}, I_{si},$ and $I_p$ are calculated by the following formulas:

$$I_{we}=I_e \cdot (R_f+R_{we} \cdot [1-R_f]^2)+I_d;$$

$$I_{se}=I_e \cdot (R_f+R_{se} \cdot [1-R_f]^2)+I_d;$$

$$I_{wi}=I_i \cdot R_{wi}+I_d;$$

$$I_{si}=I_i \cdot R_{si}+I_d; \text{ and}$$

$$I_p=I_e \cdot (R_f+R_p \cdot [1-R_f]^2)+I_d.$$

15. The spectrometric measuring head according to claim 14;
wherein the quotient q(t) is the same value at the internal measurement location and at the external measurement location.

16. The method for recalibration according to claim 7;
wherein the quotient q(t) is the same value at the internal measurement location and at the external measurement location.

17. The method for recalibration according to claim 11;
wherein at least two external standards are selectively swiveled into the beam path of the measuring head for calibrating the measuring head before putting the measuring arrangement into operation or at determined time intervals.

18. The method for recalibration according to claim 11;
wherein the recalibration by means of internal standards and/or external standards, including black and white standards, is carried out automatically according to a previously established schedule or as needed.

19. The method for recalibration according to claim 11;
wherein the interface is provided at a bus system for data transfer and/or calibration and/or system diagnosis.

20. The method for internal recalibration according to claim 11;
wherein additional, application-specific internal standards are provided for more extensive recalibrations.

21. The method for recalibration according to claim 11;
wherein the quotient q(t) is the same value at the internal measurement location and at the external measurement location.

* * * * *